United States Patent [19]

Loch

[11] 4,055,077
[45] Oct. 25, 1977

[54] METHOD AND APPARATUS FOR THE MOISTURE MEASUREMENT OF TEXTILE WEBS

[75] Inventor: Ernst Loch, Uster, Switzerland

[73] Assignee: Zellweger Uster AG, Uster, Switzerland

[21] Appl. No.: 714,846

[22] Filed: Aug. 16, 1976

[30] Foreign Application Priority Data

Oct. 2, 1975 Switzerland .................... 12780/75

[51] Int. Cl.$^2$ ............................................ G01N 27/04
[52] U.S. Cl. ........................................................ 73/73
[58] Field of Search .................... 73/73, 159; 162/263; 324/65 R

[56] References Cited

U.S. PATENT DOCUMENTS

| 2,942,352 | 6/1960 | Eicken | 324/65 R X |
| 3,384,815 | 5/1968 | Lyall et al. | 324/65 R |

*Primary Examiner*—Jerry W. Myracle
*Attorney, Agent, or Firm*—Werner W. Kleeman

[57] ABSTRACT

A method of, and apparatus for, measuring the moisture content of flat textile structures, especially textile webs, wherein the test material is guided over at least one grounded ground-electrode and at least one further electrode is applied to the test material at the side opposite such ground-electrode. The surface of the further electrode is divided into positive, grounded and negative regions.

9 Claims, 6 Drawing Figures

METHOD AND APPARATUS FOR THE MOISTURE MEASUREMENT OF TEXTILE WEBS

BACKGROUND OF THE INVENTION

The present invention relates to a new and improved method of, and apparatus for, measuring the moisture content or dampness of textile structures, especially textile webs.

The textile moisture regulators heretofore known, operating according to the conductance measuring principle, have only been able to fulfill their function to a limited extent, particularly since the use of synthetic textile fibers. Thus, the input circuit formed by a voltage divider composed of the oftentimes extremely high current-flow resistance of the textile web and a limited high ohm fixed resistor, with voltage divider ratios beginning at about 1:100 and 100:1 no longer allow for any signal evaluation. The resistances which are standard with synthetic textiles, up to approximately $10^{12}$ ohms, result in voltage divisions which are greater by a number of decades than those indicated. A corresponding increase of the fixed resistance, as a general rule, cannot be realized due to the limited resistance of the insulating material and the amplifier inputs.

Apart from these limitations of the measurement range there also come into play the ripple or noise due to the extremely high ohmic and long infeed lines as well as falsification of the measuring signal by fault or error currents, caused by the high static charges of the moved textile webs. These discharge currents are oftentimes of the same order of magnitude or even greater by several picoamperes, than the measuring currents conventional for dry synthetics, and thus, make it impossible to carry out reliable measurement of such materials.

SUMMARY OF THE INVENTION

Hence, it is a primary object of the present invention to provide an improved method of, and apparatus for, measuring the moisture content of textile articles, especially textile webs, in a manner not associated with the aforementioned drawbacks and limitations of the prior art proposals.

Another and more specific object of the present invention aims at the provision of a novel method of, and apparatus for, measuring the moisture content of textile materials in an extremely reliable, accurate and relatively simple manner.

Now in order to implement these and still further objects of the invention, which will become more readily apparent as the description proceeds, the method for measuring the moisture content of textile materials, especially textile webs, contemplates guiding the textile material defining a test material over at least one grounded-ground electrode, applying at least one further electrode to the test material at the side opposite such ground electrode, and subdividing the surface of the further electrode into positive, grounded and negative regions.

The invention is also concerned with an apparatus for the performance of the aforesaid method which comprises an electrode arrangement wherein at least a grounded electrode is arranged at one side of the test material, and at least one further electrode is arranged at the other side of the test material, and the surface of the further electrode is subdivided into zones of different potential.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
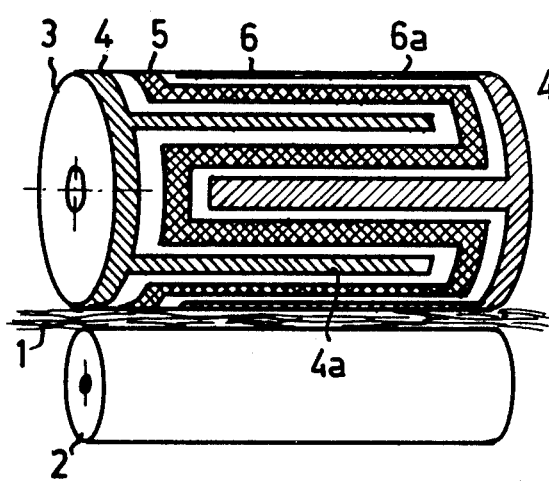
FIG. 1 illustrates the test material with electrodes applied to both sides.

Describing now the drawings, in the illustration of the principle measurement arrangement according to FIG. 1, the test material 1 in the form of for instance a substantially flat textile structure is guided between substantially cylindrical electrodes, wherein reference character 2 designates a ground electrode and reference character 3 a measuring electrode. The ground electrode 2 is in the form of a metallic grounded cylinder. The measuring electrode 3 consists of a cylinder, the surface of which is partially provided with metallic layers 4, 5 and 6. The layers 4 and 6 mesh in a comb-like fashion with one another by means of their combs or teeth 4a, 6a, respectively, and the layer or covering 5 extends in a meander-shaped or undulating manner between the comb teeth 4a and 6a over the cylinder periphery. The layer or covering 4 is, for instance, of positive polarity, the layer or covering 5 grounded and the layer or covering 6 has negative polarity. Consequently, the surface of the test material 1 is subdivided into relatively narrow zones, wherein the static surface charge is conducted away at least at the region of the grounded covering or layer 5.

Figure 2:
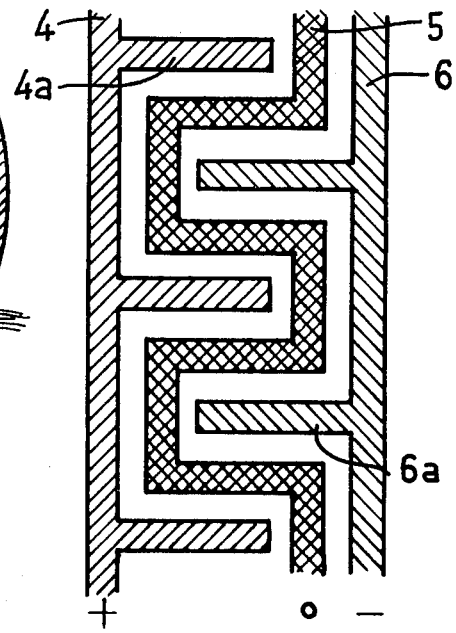
FIG. 2 is a development view of an electrode according to the present invention.

FIG. 2 illustrates a portion of the development of the measuring electrode 3, wherein there will be clearly recognized the electrode arrangement.

Figure 3:
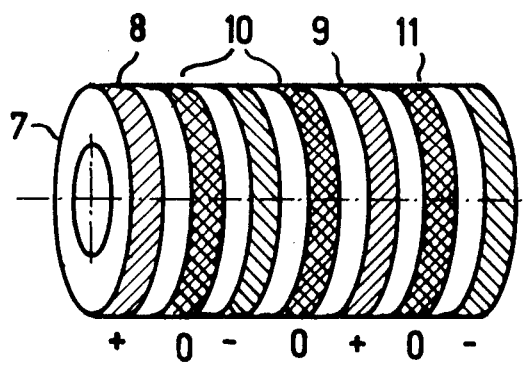
FIG. 3 illustrates a further shape of electrode.

FIG. 3 illustrates another measuring electrode 7 wherein the zones of different polarity are formed by arranging disks next to one another in a row. Thus, for instance there are provided positive disks 8, negative disks 9 and grounded disks 10, which are alternately separated by insulating disks 11. In this case the surface of the test material 1 is divided in its lengthwise direction into strips, and in each instance the one beneath the grounded disk 10 is statically discharged.

Figure 4:
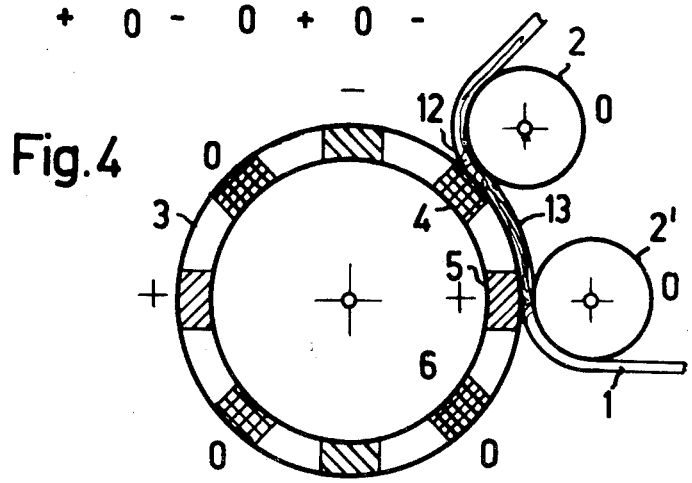
FIG. 4 schematically illustrates the course of the electrical field in the test material.

FIG. 4 schematically illustrates the approximate course of the electrical field in cross-section of the test material 1, when the measuring electrode 3 bears at one side of the test material and two ground electrodes 2, 2' bear at the other side and the test material partially wraps around the measuring electrode 3. It will be seen that initially a field 12 extends transversely through the test material, where the ground electrodes 2, 2' are disposed opposite a voltage-carrying electrode located at the periphery of the ground electrode 3.

Additionally, a further field 13 passes through the test material 1 in its lengthwise direction, namely from the voltage-carrying electrodes 4, 6 to the intermediately situated ground electrode 5. By means of this field distribution there is achieved the result that the moisture measurement becomes independent of the thickness of the test material, at least over a limited range. The conductivity of the test material 1 in the transverse direction increases with decreasing thickness, but decreases in the lengthwise direction of the test material. Even if such opposed tendencies of the conductivity do not exactly compensate one another, still there is to be expected that the measurement of the moisture content will be less affected by the material thickness.

Figure 5:
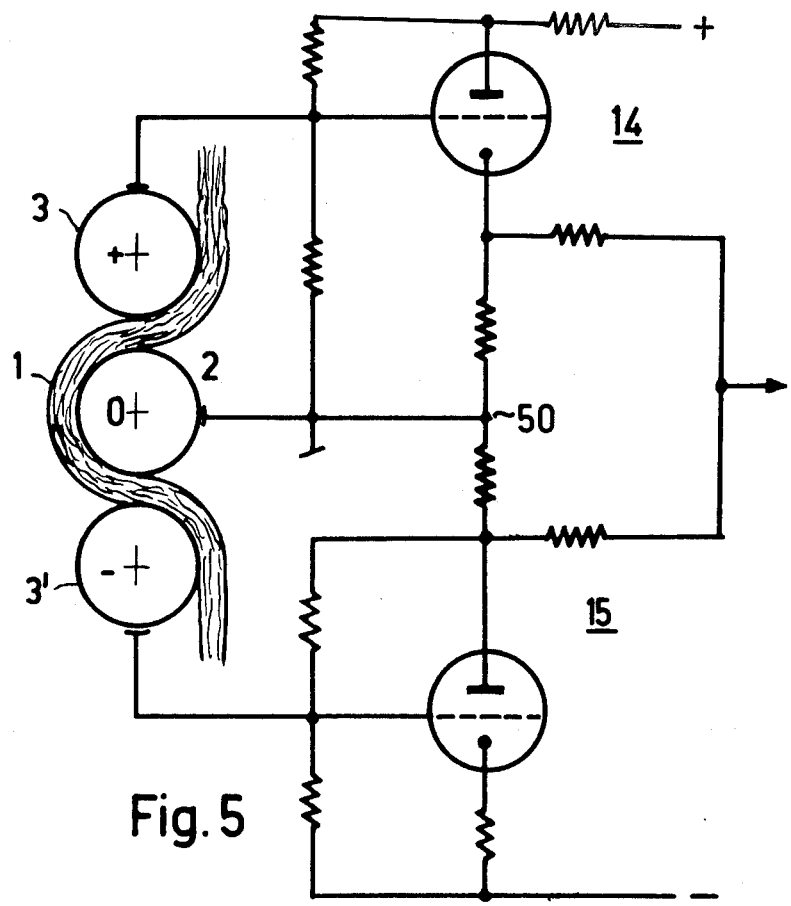
FIG. 5 is a schematic circuit diagram of apparatus for the measurement of the moisture content of the textile structures.

FIG. 5 illustrates circuitry for the moisture measurement. The test material 1 is guided over the active electrodes 3, 3' and the ground electrode 2. The active electrodes 3, 3' are positively and negatively polarized with respect to ground. Instead of both active electrodes 3, 3' there also could be used only a measuring electrode according to FIG. 1 or FIG. 3, and the positive polarity applied at the one comb-shaped covering 4, the negative polarity at the other comb-shaped covering 6 and the meander-shaped covering 5 grounded. The active electrodes 3, 3' are each electrically coupled with the inputs or input terminals of the amplifiers 14, 15 respectively which are connected in cascade circuit arrangement. The ground electrode 2 and possibly also the ground region 5 of the measuring or active electrodes 3, 3' are connected with the center tap or point 50 of the cascade arrangement. These amplifiers 14, 15 add the currents caused by the conductivity of the test material in the lengthwise and transverse directions, whereas for instance, fault or disturbance currents, emanating from the residual static charge, mutually eliminate one another and are not contained in the output signal. This constitutes a notable advantage of the inventive arrangement.

Figure 6:
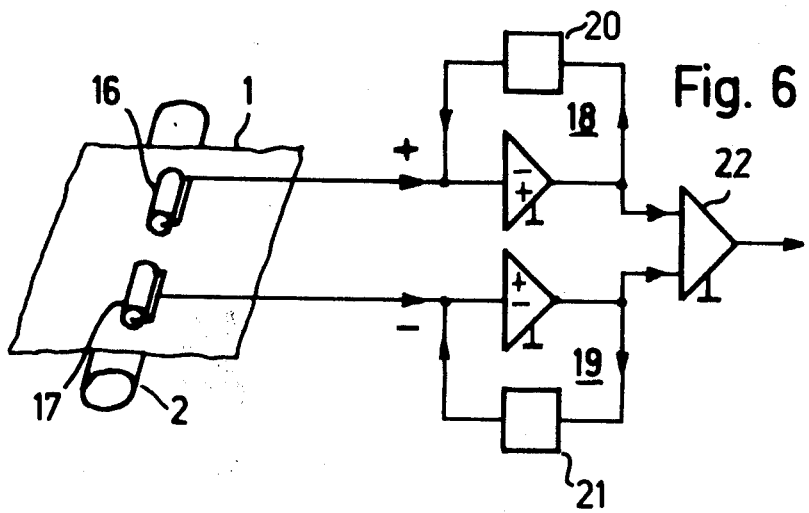
FIG. 6 illustrates another measuring arrangement for moisture measurement.

Finally, FIG. 6 illustrates a simplified measuring arrangement which is suitable for less demanding measurement functions. With this arrangement the test material 1 is guided over a grounded-ground electrode 2. Bearing at the test material 1 are two electrodes 16, 17 which are polarized differently with respect to ground, and constructed as simple cylinders with metallic surfaces. These polarized electrodes 16, 17 are connected with the input terminals of operational amplifiers 18, 19 provided with feedback devices 20, 21 and the output voltage of such amplifiers is delivered to a further amplifier 22. Also in this arrangement disturbance or interfering voltages emanating from the surface charges are eliminated and the measuring signal constitutes the sum of the individual values between the polarized electrodes 16, 17 and the measuring electrode 2.

While there are shown and described present preferred embodiments of the invention, it is to be distinctly understood that the invention is not limited thereto, but may be otherwise variously embodied and practiced within the scope of the following claims. Accordingly,

What is claimed is:

1. A method of measuring the moisture content of textile material, comprising the steps of guiding the textile material forming a test material over at least one grounded-ground electrode, applying at least one measuring electrode to the side of the test material opposite the ground electrode, dividing the surface of the measuring electrode into positive, grounded and negative regions, and measuring the conductivity of the textile material between the ground electrode and the measuring electrode.

2. The method as defined in claim 1, wherein the conductivity of the test material is measured both in its transverse direction and in its lengthwise direction.

3. The method as defined in claim 1, including the step of at least partially removing by means of parts of the measuring electrode the static surface charges during the measuring operation, and said measuring of the conductivity of the textile is carried out by applying a measuring voltage between the ground electrode and the measuring electrode.

4. The method as defined in claim 1, including the step of connecting the measuring electrode with amplifier means connected in a cascade circuit arrangement and connecting the ground electrode and the grounded region of the measuring electrode with the center point of the cascade circuit arrangement.

5. The method as defined in claim 4, including the step of guiding the test material between the ground electrode and two active electrodes possessing opposite polarity.

6. An apparatus for measuring the moisture content of textile structures, comprising an electrode arrangement embodying at least one ground electrode at one side of the textile material defining the test material and at least one further electrode at the other side of the test material, said further electrode having a surface divided into zones of different potential, and amplifier means for measuring the current between said ground electrode and said further electrode.

7. The apparatus as defined in claim 6, wherein the further electrode possesses a surface comprising comb-like configured metallic conductive zones and a meander-shaped grounded zone.

8. The apparatus as defined in claim 7, wherein the further electrode is arranged opposite the ground electrode and is located at the other side of the test material.

9. The apparatus as defined in claim 6, further including a cascade arrangement of amplifiers having inputs and a center point, the further electrode being connected with the inputs of the amplifiers and the ground electrode being connected with the center point.

* * * * *